United States Patent [19]

Pasternak et al.

[11] Patent Number: 4,878,493
[45] Date of Patent: Nov. 7, 1989

[54] HAND-HELD DIATHERMY APPARATUS

[75] Inventors: Eliezer Pasternak; Robert C. Drews; Tadmor Shalon, all of St. Louis County, Mo.

[73] Assignee: Ninetronix Venture I, St. Louis, Mo.

[21] Appl. No.: 815,661

[22] Filed: Dec. 30, 1985

Related U.S. Application Data

[63] Continuation of Ser. No. 546,571, Oct. 28, 1983, abandoned.

[51] Int. Cl.[4] ............................................. A61B 17/39
[52] U.S. Cl. ........................... 128/303.14; 128/303.17; 128/801; 219/234
[58] Field of Search .................. 128/303.13, 303.14, 128/303.17, 303.18, 800, 801; 219/234, 240

[56] References Cited

U.S. PATENT DOCUMENTS

| 1,814,791 | 7/1931 | Ende | 128/303.17 |
| 2,894,512 | 7/1959 | Tapper | 128/303.18 |
| 3,054,405 | 9/1962 | Tappe | 128/303.18 |
| 3,197,612 | 7/1965 | Reich | 128/303.14 X |
| 3,478,744 | 11/1969 | Leiter | 128/303.14 |
| 3,658,067 | 4/1972 | Bross | 128/303.14 |
| 3,934,115 | 1/1976 | Peterson | 128/303.14 |
| 4,033,356 | 7/1977 | Hang | 128/801 X |
| 4,531,524 | 7/1985 | Mioduski | 128/303.13 |

FOREIGN PATENT DOCUMENTS 171157  5/1952  Fed. Rep. of Germany ........................ 128/303.18

Primary Examiner—Lee S. Cohen
Attorney, Agent, or Firm—Flehr, Hohbach, Test, Albritton & Herbert

[57] ABSTRACT

A hand-held or portable diathermy apparatus is disclosed comprising a housing, a battery power supply preferably within the housing, and at least one electrode carried by the housing. The apparatus includes a radio frequency power generator for generating an oscillatory current ranging between about 1 kilohertz and about 20 megahertz, and supplying this oscillatory current to the electrodes. A manually operated switch is carried by the housing for selective energization of the radio frequency generator whereby, upon energization thereof, the apparatus is capable of being cycled several times outputting up to about 20 watts of power for up to 20 seconds or more on each cycle.

3 Claims, 2 Drawing Sheets

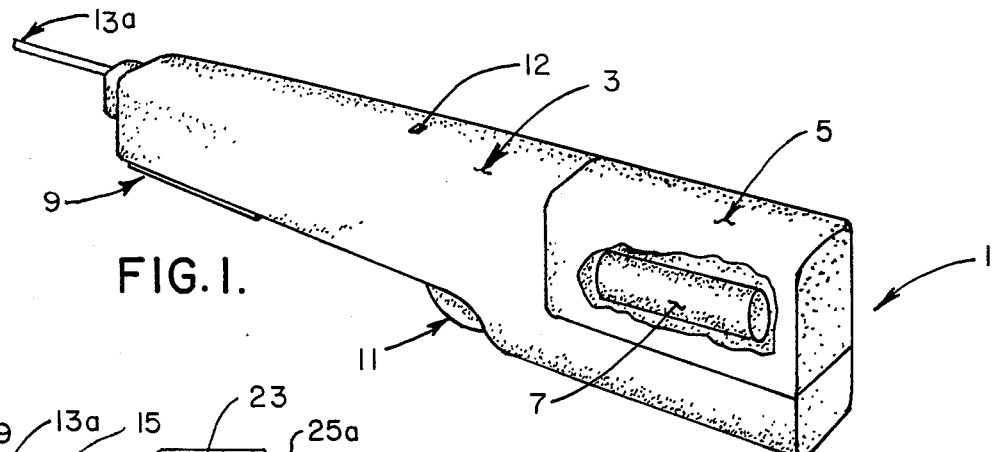
FIG. 1.
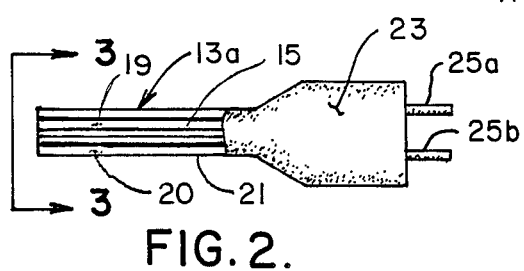
FIG. 2.
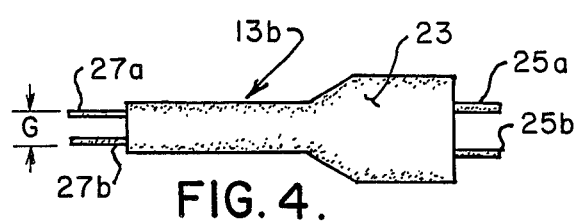
FIG. 4.
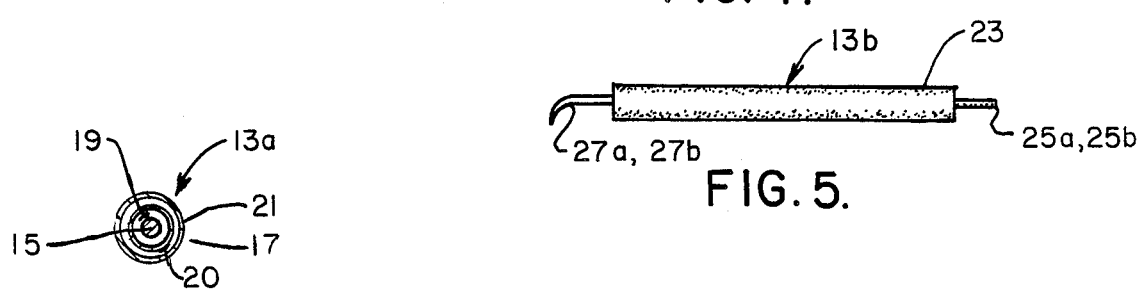
FIG. 5.
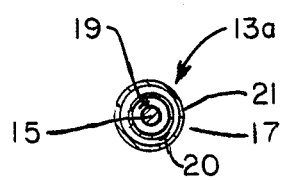
FIG. 3.
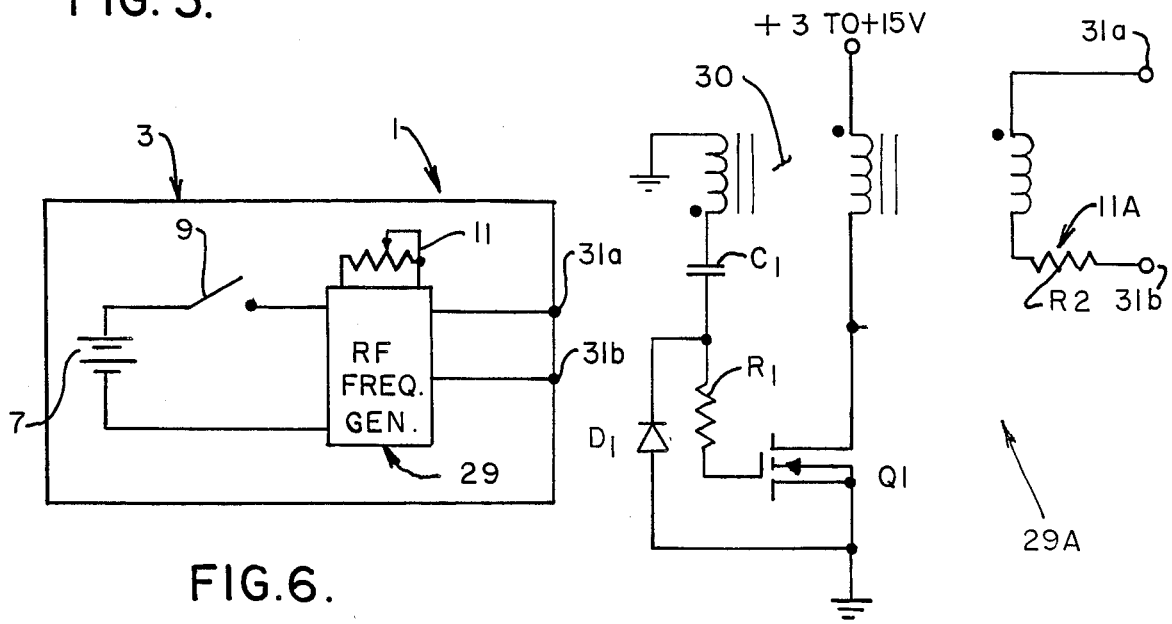
FIG. 6.
FIG. 7.

HAND-HELD DIATHERMY APPARATUS

This is a continuation of application Ser. No. 546,571 filed Oct. 28, 1983, now abandoned.

BACKGROUND OF THE INVENTION

This invention relates to diathermy apparatus, and more particularly to a diathermy hand piece in which at least the radio frequency generating portion of the power supply is carried within the hand piece so as to be in close proximity to the electrode working tips or electrode.

More generally, diathermy is a medical treatment in which heat is produced internally within the tissue of the patient by exposing the tissue to a high frequency oscillatory electrical current via a pair of energized electrodes or the like. The principles of diathermy medical treatment are typically utilized for electrocoagulation in which a mono- or bi-polar coagulator or forceps is used for hemostasis. By utilizing bi-polar coagulators, pinpoint hemostasis of tiny bleeders in the operating field is possible with minimal effects on surrounding tissue. Since thermal heat is not used for diathermy cauterization purposes, diathermy coagulation is usable in a wet operating field, whether used in conjunction with a saline irrigation agent or whether the operating field is bloody. The advent of such bi-polar diathermy coagulator apparatus has led to many medical advances in neurological and microsurgical techniques because it is now possible to effectively restrict the area of tissue damage. It will be understood that the general principle of diathermy coagulation is that by heating the tissue, the tissue proteins are coagulated thus stopping bleeding. By using carefully controlled diathermy coagulator apparatus, charring and other excessive heating of the tissue surrounding the bleeders is minimized.

Several years ago, upon the introduction of diathermy techniques, radio frequency generators were used to energized the coagulators. Typically, these radio frequency generators were quite large in size and were located remotely from the mono-polar or bi-polar forceps or hand piece. The radio frequency energy generated by the radio frequency generator was carried to the hand piece by elongate electrical leads or the like. In many early diathermy instruments, a quenched spark gap transmitter was utilized as the radio frequency generator. The wave forms generated by such quenched spark gap power supplies were of fairly high voltage which resulted in relatively deep tissue penetration and were intermittent such that little heat was generated and such that each cycle produced only a small degree of coagulation. Thus, as compared to heated wire cauterization apparatus, a uniform heat at a predetermined tissue depth produced less heat with more coagulation, provided more control for the surgeon, and resulted in less charring and other damage to the surrounding tissue.

As mentioned, the radio frequency generators of prior art diathermy apparatus were located remotely from the electrodes utilized by the surgeon and the electrodes were connected to the radio frequency generator by relatively long electrical lead wires. Because of the large size of the radio frequency generator, it was often difficult to find space for the radio frequency generator in a crowded operating room. Also, because of the large size of the radio frequency generator and the type of equipment (i.e., an oscillatory radio frequency source), it was difficult to sterilize the radio frequency generator without causing damage to the generator or without applying harmful chemicals. Also, by energizing the electrodes with high frequency radio frequency energy via long lead lines, various capacitive loads were impressed on the radio frequency output which in turn required the radio frequency generator to emit more power than was necessary for diathermy treatment of the patient. This inefficiency in radio frequency generators has resulted in increased danger to the patient and in increased radio frequency interference with other electronical equipment now commonly utilized in the modern operating room. Further, many prior art diathermy coagulators, referred to as mono-polar coagulators, required that the patient be grounded by a suitable grounding pad. Also, as was conventional, prior art diathermy coagulators were typically activated by means of a foot switch actuated by the surgeon. It was found that in various microsurgery applications, the requirement of a foot switch was awkward and often required the surgeon to change his body position from a desired position while performing neurological or microsurgery.

SUMMARY OF THE INVENTION

Among the several objects and features of the present invention may be noted the provision of a diathermy apparatus in which the requirement of bulky, remotely located radio frequency power supply is omitted;

The provision of such a diathermy apparatus, as for use for electrocoagulation and surgical cutting, which is energized at a frequency so as to minimize capacitive load losses between the radio frequency generator and the electrodes;

The provision of such a diathermy apparatus which reduces radio frequency emissions in the operating room which may have a deleterious effect on other operating room electronic equipment;

The provision of such diathermy apparatus which can readily accommodate a wide variation in impedance and capacitance levels in living tissues, and may be readily, selectively adjusted by the surgeon without movement from his operating position relative to the patient;

The provision of such diathermy apparatus which may be readily sterilized and maintained in a sterile condition (as by sealing it in a plastic bag or the like) until needed by the surgeon;

The provision of such diathermy apparatus which lessens the likelihood of forming standing waves in the leads between the radio frequency power source and the electrodes which could result in undesired side effects for the patient, which readily allows variations in wave forms so as to best suit the conditions of the tissue being treated, and which eliminates or significantly lessens the danger of electrocution both to the patient and to the surgeon; and The provision of such diathermy apparatus in which at least the radio frequency generator and preferably the power supply are self-contained in the hand piece thus making the diathermy apparatus of the present invention compact, making the instrument easily maneuverable by the surgeon, eliminating the requirement of elongate electrical leads or cords, making the instrument light in weight, and providing an instrument which is highly and accurately movable by the surgeon in the operating field, and in which all controls for energization and de-energization and varying the intensity and frequency of the radio frequency energy applied to the tissue may be readily controlled by controls carried by the hand piece.

Other objects and features of this invention will be in part apparent and in part pointed out hereinafter.

Briefly stated, a hand-held medical diathermy treatment apparatus of the present invention comprises a housing, a power supply, and at least one electrode carried by the housing. Further, means is supplied with electrical power from the power supply for generating a radio frequency oscillatory current ranging between about 1 kilohertz to about 20 megahertz to the above-mentioned electrode. At least a portion of the radio frequency generator means is located within the handle and a manually operable switch is carried by the housing for selective energization of the radio frequency generator means whereby, upon energization, the apparatus is capable of cycling a plurality of times outputting up to about 20 watts of power on each cycle for a time sufficient to perform desired treatment (e.g., up to 20 seconds or more).

BRIEF DESCRIPTION OF THE DRAWINGS

FIG. 1 is an isometric view of a hand-held or portable diathermy treatment hand piece of the present invention;

FIG. 2 is a side elevational view of a coaxial bi-polar electrode probe adapted to be plugged into the hand piece shown in FIG. 1;

FIG. 3 is an end view of the electrode assembly shown in FIG. 2, taken along 3—3 of FIG. 2, with the scale of FIG. 3 being somewhat enlarged for purposes of clarity;

FIG. 4 is a top plan view of an alternative arrangement of a pair of bi-polar electrodes utilizing tweezer-type or forceps-type electrode tips;

FIG. 5 is a side elevational view of the electrode assembly shown in FIG. 4;

FIG. 6 is a block diagram view of the major components of the hand held diathermy apparatus of the present invention, including a battery pack power supply, an on/off switch, a radio frequency generator, a control for varying the power output of the radio frequency generator, and output receptacles into which the electrode probes shown in FIGS. 2–5 may be inserted;

FIG. 7 is a schematic diagram of a self-oscillating flyback converter for energizing the electrodes.

Corresponding reference characters indicate corresponding parts throughout the several views of the drawings.

DESCRIPTION OF PREFERRED EMBODIMENTS

Figure 8:
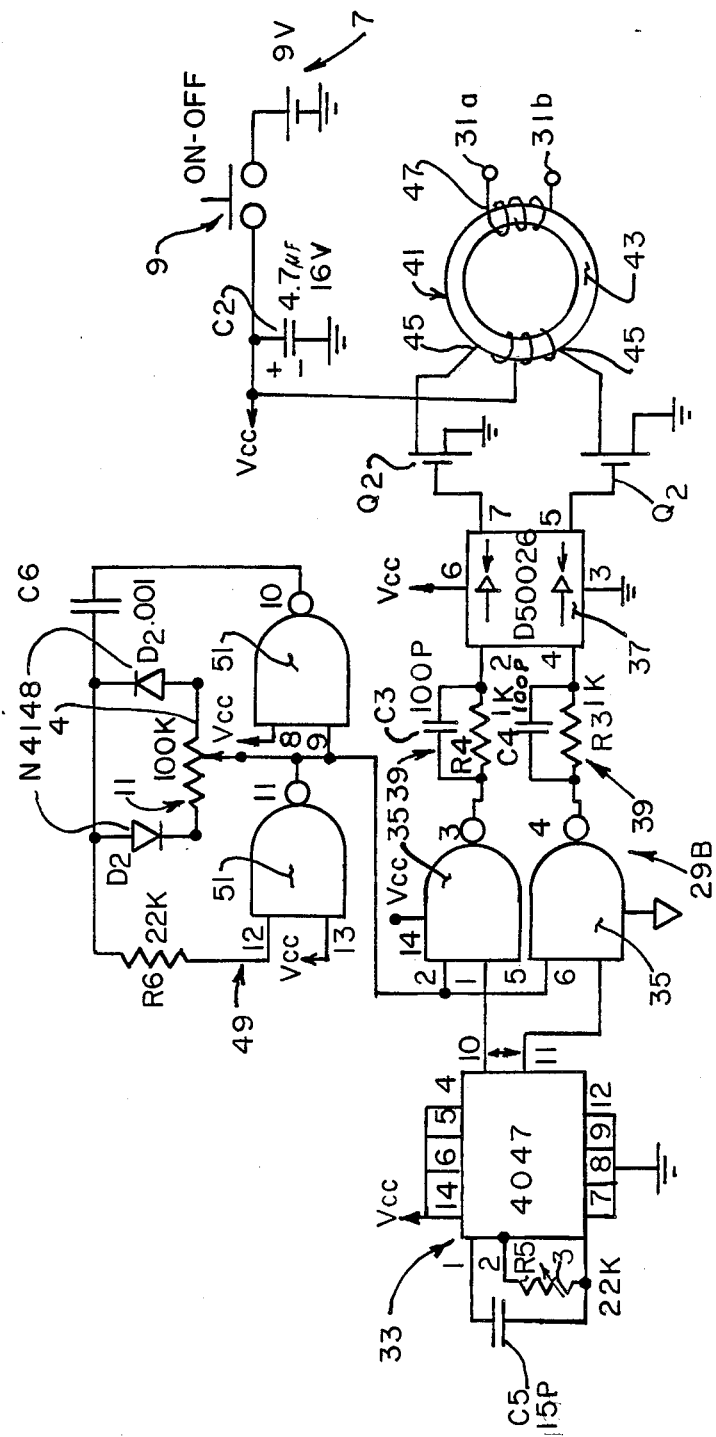
FIG. 8 is a schematic view of another radio frequency generator circuit for energizing the electrodes.

Referring now to the drawings, and particularly to FIGS. 1–5, a diathermy treatment apparatus or hand piece of the present invention is indicated in its entirety by reference character 1. The hand piece includes a housing 3 which may be readily gripped by a surgeon and which may be readily maneuvered and operated in the operating field for carrying out a variety of diathermy treatments with all of the controls (as will be hereinafter explained in detail) carried directly on the hand piece so as to facilitate operation of the hand piece by the surgeon without unnecessary detractions, such as the requirement of a foot switch for actuation of the hand piece and the like. More specifically, housing 3 is provided with a removable panel 5 providing access to one or more batteries 7 located within the housing, the batteries constituting a direct current (DC) power source for a radio frequency (RF) generator located entirely within the housing (as shown in FIG. 6) for supplying a radio frequency oscillatory current to one or more output electrodes (as will be hereinafter described in detail) for diathermy treatment. While batteries 7 are herein disclosed to be located within the hand piece housing 3, it will be understood that within the broader aspects of this invention, the direct current power supply (e.g., the batteries or an inverter) may be located remotely from the hand piece and electrically connected thereto by suitable leads. It will further be appreciated that within the broader aspects of this invention, the radio frequency generator is desirably located within the hand piece so as to minimize capacitance changes, standing wave problems, RF energy interference, and the like between a remotely located radio frequency generator interconnected to the electrodes by long leads, as was heretofore conventional. In other words, it is an object of this invention to reduce, as much as possible, the distance between the radio frequency generator and the electrodes.

Further, in accordance with this invention, hand piece 1 includes a trigger operated switch 9 readily disposed for operation by the index finger of the surgeon for energization and de-energization of the diathermy apparatus 1. A rotary switch or potentiometer 11 is provided on the hand piece which may be utilized by the surgeon for varying the power output of the radio frequency generator means in a manner as will be more particularly described in regard to the schematics shown in FIGS. 7 and 8. Also, a light indicating diode warning light, as indicated at 12, is provided for indicating the status of batteries 7. Thus, all necessary controls for the diathermy hand piece of the present invention are carried by the hand piece, and the necessity of a foot actuated switch and long power leads and switch leads are eliminated.

Referring now to FIGS. 2 and 3, a removable bi-polar electrode probe assembly, as indicated in its entirety at 13a, is provided for being plugged into the end of housing 3 for electrical connection with the radio frequency generator. More specifically, electrode probe 13a is a so-called coaxial electrode probe having a first or central coaxial electrode 15 and a second or outer electrode 17 surrounding the inner electrode 15. Intermediate electrical insulation 19 is provided between the electrodes 15 and 17. An outer layer of insulation 20 surrounds the outer electrode, and the outer insulation 20 is covered by a stainless steel sheath 21. The electrode probe assembly 13a has a body portion 23. Male electrode terminals 25a and 25b are, respectively, electrically connected to electrodes 15 and 17. Thus, the electrode assembly 13a may be readily plugged into a socket (not shown) in the left-hand end (as viewed in FIG. 1) of housing 3 so as to electrically connect the electrodes 15 and 17 to the radio frequency generator of the hand piece 1 of the present invention in a manner as will hereinafter appear. Also, in this manner, electrode probes may be readily changed by the surgeon during surgery without the necessity of complicated disassembly of the apparatus. Further, the electrode probes may be readily sterilized in any conventional manner and sealed in a sterile plastic bag or the like until ready for use.

Referring to FIGS. 4 and 5, an alternative embodiment of the electrode assembly is indicated in its entirety by reference character 13b. More specifically, electrode assembly 13b has a pair of spaced bi-polar tweezer-type electrode forcep tips 27a, 27b extending outwardly and downwardly from the end of the insulative electrode body with a gap G between the electrode tips. This type of electrode assembly is particularly well suited for bi-polar coagulation techniques.

While not shown, those skilled in the art will appreciate that a mono-polar electrode probe used in conjunction with a patient grounding mat may be used with the handpiece 1 of the present invention for mono-polar diathermy techniques, including mono-polar coagulation and surgical cutting.

Referring now to FIG. 6, the basic components of the diathermy hand piece 1 of the present invention are shown in schematic or block diagram form. More particularly, it can be seen that batteries 7 are connected in series via the on/off switch 9 to a radio frequency generator, as indicated in its entirety by reference character 29. The output (i.e., the power) of radio frequency generator 29 is selectively controlled by means of a rotary potentiometer 11. Further, the output of radio frequency generator 29 is supplied to a pair of female electrical receptacles, as indicated at 31a, 31b, for receiving the electrical terminals 25a, 25b of either electrode assembly 13a or 13b such that the electrode probes may be readily plugged into or removed from receptacles 31a, 31b.

Referring now to FIG. 7, a first detailed embodiment of the radio frequency generator 29 is illustrated in its entirety by reference character 29A. More particularly, radio frequency generator 29A is so-called self-oscillating flyback converter suitable for driving a higher voltage which utilizes the core characteristics of a transformer 30 to determine the frequency output of the generator. More specifically, a diode D1, such as an IN4148 diode, prevents negative spikes from occurring at the VMOS gate of a power transistor Q1. Resistor R1 may be, for example, a 100 ohm resistor and is used as a parisitic suppressor. Capacitor C1 may, for example, have a capacitive value of about 0.1 microfarads. With the transformer shown, such as is commercially available from Indiana General of Valparaiso, Indiana, under the trade designation F626-12-Qz, the operating frequency of the frequency generator 29A is about 250 kilohertz. As indicated, the voltage source supplied to one of the terminals may vary between about 3 and 15 volts. Accordingly, batteries 7 of the present invention may range from a plurality of AA size conventional alkaline batteries to one or more conventional D size alkaline batteries, depending on the desired power output of the device and the number of repeated operations desired before it is necessary to change the batteries.

In FIG. 8, still another embodiment of another radio frequency generator is indicated in its entirety by reference character 29B. Generally, batteries 7 are connected in series by means of the selectively operable, on/off switch 9 to an oscillator circuit, as generally indicated at 33, which generates a square wave at, for example, a frequency of about 500 kilohertz. The outputs of oscillator 33 are driven in opposite polarities and are supplied to output transistors Q2, such as IRF532 transistors, commercially available from International Rectifiers, El Segundo, California, via NAND gates 35 and a MOS driver 37 with a speed-up RC circuit 39 interposed between the NAND gates 35 and the MOS driver 37. A toroid transformer 41 having a toroidal core 43 is driven in a push-pull manner by transistors Q2. More specifically, the toroid transformer 41 has a double primary 45, with each primary 45 consisting of 7 windings, and a secondary winding 47 having 35 windings. The toriod may, for example, be a type 204T250-3C8, commercially available from Ferroxcube of Saugerties, New York. The secondary winding 47 of transformer 41 is directly connected to the output terminals 31a and 31b of the hand piece. The power output is controlled by sequentially gating the two NAND gates 35 "on" and "off" at a variable duty cycle by means of a variable duty cycle oscillator 49 at a frequency far below the frequency of oscillator 33. Variable duty cycle oscillator 49 comprises two NAND gates 51 interconnected to the power output adjustment switch 11.

In actual operation, a hand-held diathermy apparatus 1 of the present invention utilizing the frequency generator power supply, as generally indicated at 8, was successfully used in opthalmalic operations as a bi-polar coagulator for small blood vessels. This device produced up to 4 watts of power for several short periods up to about 10 seconds each from two standard "C" size alkaline batteries 7. In other tests, the apparatus delivered about 4 watts of power into a 500 ohm load (not shown) which was found to be sufficient for coagulation of small blood vessels.

Batteries 7 with higher power densities and yet of reasonable physical size and weight are available. For example, two "C" size battery cells, such as model CSC933B30, commercially available from Electrochem Industries, Inc., of Clarence, New York, deliver about 16 watts of power for several short periods of about 10 seconds each. It has been found that this power can fulfill several applications for surgical diathermy.

It will be appreciated that if still higher power outputs are required for the radio frequency generator, the battery or DC power supply may be separated from the hand piece and connected to it by lead wires. Since only DC current is flowing through the above-mentioned lead wires, the capacitive changes and standing wave phenomena, heretofore disclosed as a problem in regard to prior diathermy apparatus in which the radio frequency generator was located remotely from the hand piece, is eliminated.

Also, those skilled in the diathermy art will recognize that it will be possible to utilize the hand piece 1 of the present invention as a uni-polar coagulator in which case one of the two output terminals 31a, 31b is attached to a ground plate electrode (not shown) in electrical contact with the patient's body, and the other electrode is connected to the coagulating hand piece. Also, by utilizing higher radio frequency energy, for example, about 13 megahertz, a single electrode usable for cutting procedures is feasible.

It will also be understood that electrodes 13a or 13b may be readily sterilized in any conventional manner and sealed in a plastic bag or the like ready for use. Also, hand piece 1 is preferably made of sanitary construction such that after surgery it may be readily cleaned and sterilized, such as with suitable gas, and sealed in a bag for use.

Generally, the term "diathermy" is herein used in a broad and not in a limiting sense. For example, it will be appreciated that this apparatus and method may be utilized for conventional diathermy bi-polar and uni-polar coagulation procedures, and for other applications. In particular, the apparatus of this invention, having a radio frequency output ranging between about 1 kilohertz to microwave frequencies, may be utilized for the treatment of living tissues by integrating at least the output stage of the radio frequency generator 29 into the hand piece. It will be further appreciated that when such higher frequency radio frequency energy is utilized (i.e., radio frequencies having a wavelength shorter than about 1 meter or less), many of the standing wave problems typically associated with prior art diathermy apparatus in which the radio frequency generator is located remote from the hand piece and connected thereto by elongate lead wires is eliminated because the distance from the radio frequency generator 29 of the present invention and the electrodes 15 and 17 is considerably less than the wavelength of the radio frequency energy.

In view of the above, it will be seen that the other objects of this invention are achieved and other advantageous results obtained.

As various changes could be made in the above constructions without departing from the scope of the invention, it is intended that all matter contained in the above description or shown in the accompanying drawing shall be interpreted as illustrative and not in a limiting sense.

We claim:

1. A hand held, cordless diathermy apparatus for use in neurological and microsurgical applications comprising an elongated housing shaped for manual support and manipulation during neurosurgery and microsurgery, an electrical power supply within said housing, radio frequency generating means within said housing and supplied with energy from said power supply for generating an oscillatory current, at least one electrode extending from one end of said housing, and switch means mounted to said housing near said one end and operable by a hand holding said apparatus during surgery, said switch means controlling the supply of said oscillatory current to said at least one electrode.

2. Apparatus as defined by claim 1 wherein said radio frequency generating means comprises a square wave oscillator having a frequency ranging between about one kilohertz to about 20 megahertz, a variable duty cycle oscillator having a frequency less than said frequency of said square wave oscillator, gate means receiving outputs from said square wave oscillator and said variable duty cycle oscillator and producing an output signal in response thereto, and power output means operably controlled by said output signal from said gate means.

3. Apparatus as defined by claim 2 and including a manually operable potentiometer carried by said housing and electrically associated with said variable duty cycle oscillator for controlling the duty cycle thereof.

* * * * *